United States Patent [19]

Yerushalmi et al.

[11] Patent Number: 5,780,641
[45] Date of Patent: Jul. 14, 1998

[54] STABILIZATION OF HALOGENATED DIALKYL HYDANTOINS

[75] Inventors: Moshe Yerushalmi; Zvi Vainberger; Shimon Herbet; James Rasco, all of Beer-Sheva, Israel

[73] Assignee: Bromine Compounds Ltd., Beer-Sheva, Israel

[21] Appl. No.: 769,542

[22] Filed: Dec. 19, 1996

[30] Foreign Application Priority Data

Dec. 25, 1995 [IL] Israel ........................... 116545

[51] Int. Cl.[6] .................. C07D 233/84; C07D 233/86; D06L 3/00; A62D 5/00; C11D 7/00; C11D 7/32
[52] U.S. Cl. ............... 548/320.5; 8/107; 252/102; 252/174; 252/542; 252/543
[58] Field of Search ............... 548/320.5; 8/107; 252/102, 174, 542, 543

[56] References Cited

U.S. PATENT DOCUMENTS

| 2,430,233 | 11/1947 | Magill | 548/320.5 X |
|---|---|---|---|
| 2,779,764 | 1/1957 | Paterson | 548/320.5 |
| 2,795,556 | 6/1957 | Quinn | 548/320.5 X |
| 2,868,787 | 1/1959 | Patterson | 548/320.5 X |
| 2,920,997 | 1/1960 | Wolf et al. | 548/320.5 X |
| 2,934,451 | 4/1960 | Prichard | 548/320.5 X |
| 2,971,959 | 2/1961 | Waugh et al. | 548/320.5 |
| 2,971,960 | 2/1961 | Waugh et al. | 548/320.5 |
| 2,986,555 | 5/1961 | Paterson | 548/320.5 |
| 3,121,715 | 2/1964 | Waugh et al. | 548/320.5 X |
| 3,147,219 | 9/1964 | Paterson | 548/320.5 X |
| 3,345,371 | 10/1967 | Paterson | 548/320.5 X |
| 3,352,860 | 11/1967 | Hass et al. | 548/320.5 X |
| 3,412,021 | 11/1968 | Paterson | 548/320.5 X |
| 4,532,330 | 7/1985 | Cole | 548/320.5 |
| 4,560,766 | 12/1985 | Girard et al. | 548/320.5 |
| 4,654,424 | 3/1987 | Girard et al. | 548/320.5 |
| 4,677,130 | 6/1987 | Puzig | 548/320.5 X |
| 4,681,948 | 7/1987 | Worley | 548/320.5 X |
| 4,698,165 | 10/1987 | Theyson | 548/320.5 X |
| 4,745,189 | 5/1988 | Lee et al. | 548/320.5 X |

FOREIGN PATENT DOCUMENTS

394 529   10/1990   European Pat. Off. .

OTHER PUBLICATIONS

1980, Kirk–Othmer Encyclopedia of Chemical Technology, vol. 12, pp. 704–705, Interscience.

Mar. 20, 1995, Chemical Abstracts, vol. 122, No. 12, Columbus, Ohio, U.S.; abstracts No. 141936, Malshe V.C. et al.: "A process for preparting a slow and constant halogen releasing material" and IN 171 574 (Ion Exchange Ltd.; India (IN) Nov. 21, 1992.

Oct. 14, 1996, Chemical Abstracts, vol. 125, No. 16, Columbus, Ohio, U.S..; abstracts No. 199132 Takanashi K. et al.: "Bacterial clarifier compositions generating no halogen gases" and JP 08 165 497 A (Kao Corp; Japan) Jun. 25, 1996.

*Primary Examiner*—Floyd D. Higel
*Attorney, Agent, or Firm*—Merchant, Gould, Smith, Edell, Welter & Schmidt, P.A.

[57] ABSTRACT

Method for stabilizing halogenated hydrantoins, comprising mixing the hydantoin with dry calcium hydroxide.

22 Claims, No Drawings

STABILIZATION OF HALOGENATED DIALKYL HYDANTOINS

FIELD OF THE INVENTION

This invention is directed to a method for stabilizing halogenated alkyl-hydantoins (hereinafter designated sometimes as "DHDAH"), to a method for storing the same, particularly after packaging them in either powder, granular or tablet form, to compositions of matter comprising stabilized DHDAH, and to stable, shape retentive products comprising DHDAH as a halogen donor.

BACKGROUND OF THE INVENTION

The halogenated alkyl-hydantoins to which this is invention is particularly directed have the general formula

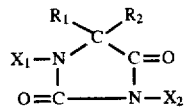

wherein $R_1$ and $R_2$ are lower alkyl groups, i.e., $C_1$–$C_4$ alkyl groups, and $X_1$ and $X_2$ are Br or Cl, independently.

A number of halogenated alkyl-hydantoins are well-known for their bleaching and disinfecting properties. Their effectiveness in these applications is due to their ability to generate (release) positive halogen in aqueous solution. Typical alkyl-hydrantoins are, for example, 5,4-dimethyl-hydantoin, 5-ethyl-5-methyl-hydantoin and 5,5-diethylhydantoin. Typical halogenated alkyl-hydantoins are the dichloro-, dibromo- and chlorobromo- derivatives of said alkyl-hydantoins.

In many applications, it is desirable to press the halogenated hydantoins in a shape retentive form, i.e., as a granule, tablet or briquette, due to the inherently irritating and dusty nature of the compounds.

Halogenated alkyl-hydantoins (e.g., 1,3-dibromo-5,5-dimethylhydantoin, 1-bromo-3-chloro-5,5-dimethyldantoin and 1,3-dichloro-5,5-dimethylhydantoin) are halogen donors typically utilized for various purposes. Thus, 1-bromo-3-chloro-5,5-dimethylhydantoin is used form swimming pool sanitizers, while 1,3-dichloro-5,5-dimethylhydantoin has been used successfully for bleaching (see, Kirk-Othmer, Encyclopedia of Chemical technology, Volume 12, pp. 704–705, Wiley Interscience, 1980; and U.S. Pat. No. 2,779,764).

One of the disadvantages of ordinary commercial halogenated hydantoins products is that the halogenated hydantoins tends to release free halogen with time, heat or exposure to sunlight while in storage. The release of halogen is desired in the use of the products for the water treatment in pools, spas, cooling towers, toilets and the like and in fact the action of the products is based on such release. However, release of halogen during storage results in the exposure of personnel to halogen when the containers, in which the products have been stored, are opened.

It is an object of this invention to provide a method of preparing substantially stable halohydantoin compositions. By "substantially stable" is meant herein a composition which does not decompose with evolution of halogen gas—viz. is no "degased", and therefore does not release halogen gas in a closed packing container—above acceptable limits. More precisely, a halohydantoin composition is considered substantially stable, as this expression is used in this specification and claims, when it passes the "Stability Test", hereinafter set forth.

It is another object of this invention to provide a method of storing halohydantoins, particularly after packaging them in either powder, granular or tablet form.

It is a further object of this invention to provide compositions of matter comprising stabilized halohydantoins, that are suitable for storing without undergoing degassing.

It is a still further object of this invention to provide stable, shape retentive products comprising halohydantoins as halogen donors.

Other objects and advantages of the invention will appear as the description proceeds.

SUMMARY OF THE INVENTION

According to the invention, halogenated hydantoins are stabilized by mixing therewith dry calcium hydroxide. By "dry calcium hydroxide" is meant calcium hydroxide that contains no more than 1% by weight of water. All the percentages in this specification and claims are by weight, unless otherwise specified.

The amount of $Ca(OH)_2$ used is preferably from 0.25 to 4–6% of the aggregate amount of DHDAH and $Ca(OH)_2$. Increasing the amount above 4% does not produce any substantial improvement and may cause pH problems in the operation. However, the invention will still be operative at such higher amounts and therefore there are no fixed upper limits to the amount of $Ca(OH)_2$ used, which can be as high as 12% and even higher. Further, while it is desirable to use at least 0.25% of $Ca(OH)_2$, lower amounts—e.g. as low as 0.1% and even lower—may be used while still achieving some stabilizing effect.

The halohydantoin and the $Ca(OH)_2$ should be intimately mixed to produce a homogenous product. Mechanical means for carrying out said mixing are available in the art and well known to skilled persons.

The halogenated hydantoins, to which this invention relates, are particularly, but not exclusively, alkylated, more particularly methylated hydantoins, and the halogens are bromine and/or chlorine.

The method for storing the halogenated hydantoins comprises preparing an intimate mixture of the hydantoin and $Ca(OH)_2$, and storing it in closed containers. In a form of the invention, the said method further comprises adding other ingredients to facilitate processing or for other purposes, and forming the resulting composition in shape retentive form, before storing it. The shape retentive form can be, e.g., that of briquettes, tablets or the like, or of granules. Alternatively, the composition can be stored in powder form, without further processing. The processing facilitating ingredients may be, e.g., as lubricants, binders, dissolution aids, and the like. After the hydantoin-$Ca(OH)_2$ mixture has been mixed with the processing ingredients, it is compacted and/or into tablets, briquettes, or other shape retentive forms. Whatever its final form, when the composition is stored in closed packing containers, marketed and used, the problem of halogen gas release and build-up in the containers does not arise, or arises to a significantly lower degree than in the case of the halogenated hydantoins and halogenated hydantoin formulations of the prior art.

The shape retentive forms of the composition are an aspect of the invention.

The use of $Ca(OH)_2$ as a stabilizers for halohydantoins is another aspect of the invention.

DETAILED DESCRIPTION OF PREFERRED EMBODIMENTS

The following examples illustrate but do not limit the invention and illustrate its advantages.

EXAMPLE 1

Preparation of the Stabilized Composition

The halogenated hydantoin to be stabilized is charged in dry, powder form, preferably with an average grain size comprised between 60 and 160μ, into a mixer. The mixer is a two-ton maximum load drum. It is built on its side in an elongated position. The material is top loaded. Inside the drum are 5 angled paddles, which turn counter to a continuous outer auger stripe. The outer agitator continuously pulls the material off the bottom of the drum and moves it counter to the inner material. Analysis shows that the material being mixed is homogeneous after one hour. However, the mixing is carried out for two hours. The desired percentage of $Ca(OH)_2$, previously dried to a water content below 0.5%, is also charged into the mixer. The mixer is then actuated at a speed of 23 rpm during 120 minutes, at room temperature. The environment humidity is controlled to prevent the mixture from acquiring an undesired degree of moisture. A homogeneous, powdery mixture is thus obtained. The powdery mixture may be granulated or tabletted by conventional means, if desired.

Skilled persons will easily be able to apply modified or different mixing, granulating and tabletizing techniques and equipment known in the art. All the compositions mentioned in the following examples have been prepared as described in this Example 1.

The following Examples show the improved stability of the compositions according to the invention over those of the prior art. Said stability was evaluated by determining as follows the amount of halogen released from the halogenated hydantoins. In the examples, dihalogenated dialkyl-hydantoins (indicated by DHDAH) have been used for purposes of illustration, but this should not be construed as a limitation of the invention, and the operations described could be carried out with any halogenated hydantoin.

A known amount of DHDAH was placed inside a 1 liter Erlenmeyer flask equipped with a ground glass fit flow tube and an exhaust provided with a glass fiber filter so as not to allow said DHDAH to escape from the flask into the KI solution, hereinafter mentioned. Halogen release was effected by one of the following methods:

Method A) The DHDAH was heated to various temperatures for various times, while a slow stream of $N_2$ was passed through the flask via the flow tube into a solution of 2% KI, which was then titrated with standard $NaS_2O_3$.

Method B) The DHDAH was allowed to stand in room light at room temperature for various periods of time, while a slow continuous stream of $N_2$ was passed through the flask via the flow tube into a solution of 2% KI, which was then titrated with standard $NaS_2O_3$.

Method C) The aforementioned method A was used, but the $N_2$ was not passed through until the end of the heat treatment, followed by 15 minutes cooling time.

A particular embodiment of Method C constitutes the stability test:

Stability Test

The composition to be tested, comprising the halogenated hydantoin and the $C(OH)_2$, is placed inside a 1 liter Erlenmeyer flask equipped with a ground glass fit flow tube and an exhaust provided with a glass fiber filter. The composition is heated to 80° C. for 4 hours. After 4.5 hours, a stream of $N_2$ is passed through the flask via the flow tube into a solution of 2% KI, which is then titrated with standard $NaS_2O_3$. The composition passes the stability test, and is considered "stable", as this term is to be construed in this application, if the amount of halogen determined by the titration is less than 50 ppm per 100 grams of composition tested.

A composition that passes the stability test will now show, ordinarily, any red color at the end of the test, and the observation of the color may constitute an abbreviated, though less precise, stability test. Further, a composition that passes the stability test will not, ordinarily, evolve any significant amount of halogen if it is kept at 25° C. or below.

Formulations of fresh dry DHDAH containing various concentrations of calcium hydroxide, having less than 0.5% water, were mixed to homogeneity and then subjected to various halogen evolution conditions, viz. heating and/or exposure to sunlight, and the halogen evolution determined by one of Methods A, B and C described above.

The DHDAH used in the following examples was BCDMH (1-bromo-3-chloro-5,5-dimethylhydantoin). All samples were in powder form unless specified. All percentages are by weight. All samples had a weight of 100 grams of aggregate BCDMH and $Ca(OH)_2$ in a 1 liter Erlenmeyer flask. The amount of bromine evolved is expressed in all the Tables as ppm of halogen, calculated as Br, for 100 grams of sample. Should a sample be larger, a proportionately larger number of ppm would of course be found.

EXAMPLE 2

Five samples were prepared as in Example 1 and tested according to Method A. The amount of $Ca(OH)_2$ added is shown in the following table. All samples were monitored for total halogen evolution.

TABLE I

| Sample | % $Ca(OH)_2$ | Temperature °C. | Time hr | $Br_2$ |
|---|---|---|---|---|
| 1-1 | 0 | 80 | 5 | 415 |
| 1-2 | 0.25 | 80 | 2.5 | 16 |
| 1-3 | 0.5 | 80 | 2.5 | 21 |
| 1-4 | 1 | 80 | 5 | 42.6 |
| 1-5 | 2 | 80 | 5 | 21.3 |

These data show quite clearly the drastic reduction in the halogen evolution, due to the invention, with even as little as 0.25% $Ca(OH)_2$.

EXAMPLE 3

In this example samples of stabilized BCDMH-$Ca(OH)_2$ compositions were subjected to heating and their stability was tested to determine the effect of the heating time. Four samples were prepared and tested according to Method A. The amount of $Ca(OH)_2$ used is shown in the following table.

TABLE II

| Sample | % $Ca(OH)_2$ | Temperature °C. | Time hr | $Br_2$ |
|---|---|---|---|---|
| 2-1 | 0 | 80 | 4 | 231 |
| 2-2 | 0.5 | 80 | 4 | 61 |
| 2-3 | 0 | 80 | 5 | 319 |
| 2-4 | 0.5 | 80 | 5 | 97 |

These data show that a 0.5% content of $Ca(OH)_2$ is still effective in stabilizing after five hours of heating.

EXAMPLE 4

Four samples of stabilized BCDMHA-$Ca(OH)_2$ compositions, with different amounts of $Ca(OH)_2$, were prepared and tested at 95° C. for 5 hours according to Method C. The results are shown in the following table.

TABLE III

| Sample | % Ca(OH)$_2$ | Temperature °C. | Time hr | Br$_2$ |
|---|---|---|---|---|
| 3-1 | 0 | 95 | 5 | 462 |
| 3-2 | 1 | 95 | 5 | 8.6 |
| 3-3 | 2.5 | 95 | 5 | 2.8 |
| 3-4 | 4 | 95 | 5 | 2 |

These data show that 1% Ca(OH)$_2$ is still effective in reducing halogen evolution at 95° C.

EXAMPLE 5

Four samples of each of 3 batches of BCDMH-Ca(OH)$_2$ compositions were prepared and tested according to Method C. Each set of 4 samples included one comparative sample (zero Ca(OH)$_2$) and 3 samples stabilized with Ca(OH)$_2$. The test data and results are shown in the following table.

TABLE IV

| Sample | % Ca(OH)$_2$ | Temperature °C. | Time hr | Br$_2$ |
|---|---|---|---|---|
| 4-1 | 0 | 25 | 7 | 265 |
| 4-2 | 1 | 25 | 7 | 1 |
| 4-3 | 2.5 | 25 | 7 | 0 |
| 4-4 | 4 | 25 | 7 | 0 |
| 4-5 | 0 | 25 | 7 | 383 |
| 4-6 | 1 | 25 | 7 | 0 |
| 4-7 | 2.5 | 25 | 7 | 3 |
| 4-8 | 4 | 25 | 7 | 0 |
| 4-9 | 0 | 25 | 7 | 311 |
| 4-10 | 1 | 25 | 7 | 4 |
| 4-11 | 2.5 | 25 | 7 | 3 |
| 4-12 | 4 | 25 | 7 | 0.5 |

These data show that 1% Ca(OH)$_2$ is effective in reducing the degassing effect.

EXAMPLE 6

In this example, the effect of sunlight on halogen degassing is studied. In addition to samples stabilized with Ca(OH)$_2$, other samples containing Na$_2$CO$_3$ or Mg(OH)$_2$ were prepared and tested. The samples were placed in direct sunlight. The samples were observed for the presence of halogen degassing. The resulting appearance of the flasks is defined in the following table as "no halogen observed" (NO), "slight red color" (SLIGHT), "red color" (RED), "dark red color" (DARK R).

TABLE V

| BATCH # | % Ca(OH)$_3$ | % Na$_2$CO$_3$ | % Mg(OH)$_2$ | Days | Observed |
|---|---|---|---|---|---|
| 5-1 | 0 | 0 | 0 | 3 | DARK R |
| 5-2 | 3 | 0 | 0 | 3 | NO |
| 5-3 | 0 | 3 | 0 | 3 | RED |
| 5-4 | 0 | 0 | 3 | 3 | SLIGHT |
| 5-5 | 0 | 0 | 0 | 3 | DARK R |
| 5-6 | 3 | 0 | 0 | 3 | NO |
| 5-7 | 0 | 3 | 0 | 3 | SLIGHT |
| 5-8 | 0 | 0 | 3 | 3 | SLIGHT |
| 5-9 | 0 | 0 | 0 | 1 | RED |
| 5-10 | 2 | 0 | 0 | 1 | NO |
| 5-11 | 0 | 2 | 0 | 1 | SLIGHT |
| 5-12 | 0 | 0 | 2 | 1 | SLIGHT |
| 5-13 | 0 | 0 | 0 | 2 | DARK R |
| 5-14 | 1 | 0 | 0 | 2 | NO |
| 5-15 | 0 | 1 | 0 | 2 | RED |
| 5-16 | 0 | 0 | 1 | 2 | SLIGHT |
| 5-17 | 0 | 0 | 0 | 7 | DARK R |
| 5-18 | 4 | 0 | 0 | 7 | NO |
| 5-19 | 0 | 4 | 0 | 7 | SLIGHT |
| 5-20 | 0 | 0 | 4 | 7 | RED |
| 5-21 | 0 | 0 | 0 | 7 | DARK R |
| 5-22 | 2.5 | 0 | 0 | 7 | NO |
| 5-23 | 0 | 2.5 | 0 | 7 | DARK R |
| 5-24 | 0 | 0 | 2.5 | 7 | RED |
| 5-25 | 0 | 0 | 0 | 30 | DARK R |
| 5-26 | 3 | 0 | 0 | 30 | NO |
| 5-27 | 0 | 3 | 0 | 30 | RED |
| 5-28 | 0 | 0 | 3 | 30 | RED |

These tests show that while Na$_2$CO$_3$ and Mg(OH)$_2$ show some stabilizing effect, Ca(OH)$_2$ is considerably superior.

EXAMPLE 7

In this example, the amount of degassing is determined for three batches—D, E and F—each tested in powder, granule and tablet form. Three samples of each of three batches were prepared from BCDMH and Ca(OH)$_2$ as described in Example 1 and tested according to Method C. The results of the tests are shown below

TABLE VI

| Batch | Form | % Ca(OH)$_3$ | Temperature °C. | Time hr. | Br$_2$ |
|---|---|---|---|---|---|
| D | POWDER | 2.5 | 80 | 20 | 0.4 |
| D | GRANULE | 2.5 | 80 | 20 | 0.8 |
| D | TABLET | 2.5 | 80 | 20 | .06 |
| E | POWDER | 3 | 80 | 20 | 1 |
| E | GRANULE | 3 | 80 | 20 | 1.7 |
| E | TABLET | 3 | 80 | 20 | 1.9 |
| F | POWDER | 4 | 80 | 20 | .06 |
| F | GRANULE | 4 | 80 | 20 | .14 |
| F | TABLET | 4 | 80 | 20 | .66 |

These data show that Ca(OH)$_2$ is an effective stabilizer for DHDAH, whether in powder, granular and tablet form.

EXAMPLE 8

This example shows the effect of time on the stabilizing effect of Ca(OH)$_2$, when used in conjunction with a binding agent such as boric acid. Four samples were prepared and tested according to Method A. The results of the tests are shown in the following table.

TABLE VII

| Sample | % Boric | % Ca(OH)$_2$ | Temperature °C. | Time hour | Br$_2$ |
|---|---|---|---|---|---|
| B-1 | 0 | 0 | 80 | 4 | 70 |
| B-2 | 4 | 1 | 80 | 4 | 2 |
| B-3 | 3 | 2 | 80 | 5 | 4 |
| B-4 | 2 | 3 | 80 | 5 | 4 |
| B-5 | 5 | 0 | 80 | 4 | 93 |

These data show that Ca(OH)$_2$ is effective in combination with boric acid.

While certain embodiments of the invention have been described by way of illustration, it will be apparent that the invention can be carried into practice by persons skilled in the art with many modifications, variations and adaptations, without departing from its spirit or exceeding the scope of the claims.

We claim:

1. Method for stabilizing halogenated hydantoins, comprising mixing the hydantoin with dry calcium hydroxide.

2. Method according to claim 1, wherein the calcium hydroxide contains no more than 1% by weight of water.

3. Method according to claim 1, wherein the hydantoin is selected from the group consisting of chlorinated alkyl-hydantoin, brominated alkyl-hydantoin, and mixtures thereof, wherein the chlorinated alkyl hydantoin and brominated alkyl-hydantoin have the formula

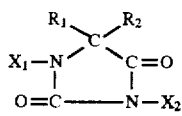

wherein $R_1$ and $R_2$ are lower alkyl groups, $X_1$ and $X_2$ are Br or Cl, independently.

4. Method according to claim 1, wherein the amount of calcium hydroxide is from 0.1% to 12% of the total composition.

5. Method according to claim 4, wherein the amount of calcium hydroxide is from 0.25% to 6% of the total composition.

6. Method according to claim 1, wherein the calcium hydroxide is intimately mixed with the hydantoin.

7. Method according to claim 1, wherein the hydantoin is chosen from among the dibromo-, dichloro- and chlorobromo-derivatives of 5,5-dimethyl-hydantoin, 5-ethyl-5-methyl-hydantoin and 5,5-diethyl-hydantoin.

8. Method for storing halogenated hydantoin, which comprises the steps of preparing an intimate mixture of the hydantoin and Ca(OH)$_2$ according to claim 1 and storing the same in closed containers.

9. Method for storing hydantoin, which comprises preparing an intimate mixture of the hydantoin and Ca(OH)$_2$, and forming the resulting composition in shape retentive form.

10. Method according to claim 9, wherein the shape retentive form is chosen from among briquettes, tablets and granules.

11. Method according to claim 9, wherein intimate mixture of hydantoin and Ca(OH)$_2$ further comprises the processing facilitating ingredients selected from lubricants, binders and dissolution aids.

12. Method according to claim 9, which comprises compacting the hydantoin-Ca(OH)$_2$ and processing ingredients mixture.

13. Method according to claim 9, which comprises forming the hydantoin-Ca(OH)$_2$ and processing ingredients into tablets or briquettes.

14. Stabilized halogenated hydantoin composition, comprising an halogenated hydantoin and Ca(OH)$_2$.

15. Composition according to claim 14, which comprises water in an amount of not more than 1% of the weight of the Ca(OH)$_2$.

16. Composition according to claim 14, which comprises additional components.

17. Composition according to claim 16, wherein the additional component is boric acid.

18. Composition according to claim 14, in shape retentive form.

19. Composition according to claim 18, wherein the shape retentive form is chosen from among briquettes, tablets and granules.

20. Composition according to claim 14, wherein the hydantoin is chosen from among 1,3-dibromo-5,5-dimethylhydantoin, 1-bromo-3-chloro-5,5-dimethyldantoin and 1,3-dichloro-5,5-dimethylhydantoin.

21. Composition according to claim 14, wherein the amount of calcium hydroxide is from 0.1% to 12% of the total composition.

22. Composition according to claim 14, wherein the amount of calcium hydroxide is from 0.25% to 6% of the total composition.

* * * * *

UNITED STATES PATENT AND TRADEMARK OFFICE
CERTIFICATE OF CORRECTION

PATENT NO. : 5,780,641

DATED : JULY 14, 1998

INVENTOR(S) : YERUSHALMI ET AL.

It is certified that error appears in the above-identified patent and that said Letters Patent is hereby corrected as shown below:

Column 3, line 61, change "C(OH)$_2$" to —Ca(OH)$_2$—.

Column 4, line 66, change "BCDMHA–" to —BCDMH– —.

Signed and Sealed this

Sixteenth Day of May, 2000

*Attest:*

Q. TODD DICKINSON

*Attesting Officer*     *Director of Patents and Trademarks*